United States Patent [19]

Oshige et al.

[11] Patent Number: 5,311,285
[45] Date of Patent: May 10, 1994

[54] MEASURING METHOD FOR ELLIPSOMETRIC PARAMETER AND ELLIPSOMETER

[75] Inventors: Takahiko Oshige; Takeo Yamada; Akira Kazama, all of Tokyo, Japan

[73] Assignee: NKK Corporation, Tokyo, Japan

[21] Appl. No.: 816,594

[22] Filed: Dec. 31, 1991

[30] Foreign Application Priority Data

Aug. 29, 1991 [JP] Japan .................................. 3-217656
Oct. 11, 1991 [JP] Japan .................................. 3-263690

[51] Int. Cl.[5] ............................................. G01B 11/06
[52] U.S. Cl. ..................................... 356/369; 356/367
[58] Field of Search ............... 356/364, 365, 366, 367, 356/369; 250/225

[56] References Cited

U.S. PATENT DOCUMENTS

| | | | |
|---|---|---|---|
| 3,556,662 | 1/1971 | Levenstein et al. | 356/365 |
| 4,850,711 | 7/1989 | Sano et al. | 356/369 |
| 4,872,758 | 10/1989 | Miyazaki et al. | 356/369 |
| 5,073,025 | 12/1991 | Brooks | 356/364 |
| 5,102,222 | 4/1992 | Berger et al. | 356/365 |

FOREIGN PATENT DOCUMENTS

| | | |
|---|---|---|
| 57-166533 | 10/1982 | Japan . |
| 61-83924 | 4/1986 | Japan . |
| 62-293104 | 12/1987 | Japan . |
| 63-36105 | 2/1988 | Japan . |
| 64-28509 | 1/1989 | Japan . |

OTHER PUBLICATIONS

Dill et al, "Ellipsometry with pulsed tunable laser sources", *IBM Technical Disclosure Bulletin*, vol. 19, No. 4 (Sep. 1976) pp. 1487–1489.
Extended Abstracts (The 52nd Autumn Meeting, 1991); The Japan Society of Applied Physics, No. 3, p. 844.
The Review of Scientific Instruments, vol. 42, No. 1, Jan. 1971, pp. 19–22.

Primary Examiner—Richard A. Rosenberger
Attorney, Agent, or Firm—Frishauf, Holtz, Goodman & Woodward

[57] ABSTRACT

Movable optical parts included in an ellipsometer are removed to increase the measurement speed, and a specific quadrant to which a phase difference $\Delta$ as an ellipsometric parameter belongs is determined by one measuring operation. A beam is radiated from a light source section onto a measurement target, and the reflected beam having an elliptically polarized beam, which is reflected by the target, is divided into four different polarized light components. The optical intensities of the respective light components are then detected. Ellipsometric parameters $\psi$ and $\Delta$ are calculated on the basis of the detected four optical intensities. In addition, the above-mentioned four different polarized light components are obtained by using a wave plate. Furthermore, the polarization directions of the four polarized light components whose optical intensities are obtained are respectively set at angles $-45°$, $+45°$, $90°$, and $0°$ with respect to a reference direction. Alternatively, a composite beam splitter is used to obtain four polarized light components.

7 Claims, 15 Drawing Sheets

5,311,285

MEASURING METHOD FOR ELLIPSOMETRIC PARAMETER AND ELLIPSOMETER

BACKGROUND OF THE INVENTION

The present invention relates to a measuring method for an ellipsometric parameter, which is designed to measure ellipsometric parameters used to measure the thickness of a thin film, and an ellipsometer for measuring ellipsometric parameters by using this measuring method.

As a method of measuring the thickness of a thin film, ellipsometry is used. In this method, a change in polarization state upon reflection of a beam by a sample surface, i.e., a ratio $\rho$ between a reflectance Rp of a light component (P component) parallel to the incident plane of an electric field vector and a reflectance Rs of a light component (S component) perpendicular thereto, is measured according to equation (1), and a film thickness d is obtained in accordance with a predetermined relationship between the already obtained polarization reflectance ratio $\rho$ and the film thickness d:

$$\rho = Rp/Rs = \tan\Psi \exp[j\Delta] \quad (1)$$

In this case, since the polarization reflectance ratio $\rho$ is normally represented by a complex number as indicated by equation (1), two ellipsometric parameters, i.e., an amplitude ratio $\Psi$ and a phase difference $\Delta$, must be obtained.

As a conventional method of obtaining these ellipsometric parameters $\Psi$ and $\Delta$, the null ellipsometry method is known. In this method, a polarized beam is radiated from a light source onto a measurement target at a predetermined angle with respect to the target, and a beam reflected by the target, which is elliptically polarized, is transmitted through a $\lambda/4$ plate and an analyzer to be guided to a light-receiving unit. While optical intensity signals obtained by the light-receiving unit are observed through, e.g., a measuring unit, the $\lambda/4$ plate and the analyzer are rotated to obtain a rotational angle at which the minimum optical intensity is observed. The above-mentioned ellipsometric parameters are calculated on the basis of this rotational angle. In this method, however, since the analyzer needs to be rotated to find an angular position at which the minimum optical intensity is observed, a measuring operation requires a long period of time.

Under the circumstances, a method using a rotating analyzer is proposed as a method of measuring the above ellipsometric parameters at a relatively high speed. More specifically, according to this method, similar to the above-described null ellipsometry, a linearly polarized beam with predetermined azimuth angle, e.g. 45°, is radiated from a light source onto a measurement target, at a predetermined angle with respect to the target, and the ellipsometric parameters are calculated on the basis of the output waveforms of optical intensity signals obtained by a light-receiving unit when the analyzer on the measurement side is rotated once.

In the measuring method for an ellipsometric parameter, which uses the rotating analyzer, however, the following problems are posed.

(1) The analyzer must be rotated once to execute one measuring operation. This rotation requires a predetermined period of time or more. Therefore, it is impossible to obtain the ellipsometric parameters $\psi$ and $\Delta$ of a measurement target which is moving at high speed and to measure the film thickness d on the basis of these ellipsometric parameters. In addition, the presence of a mechanical movable portion increases the size of the apparatus itself. For this reason, the apparatus cannot be installed on a production line in a factory to perform on-line measurement of film thicknesses on measurement targets, e.g., continuously supplied measurement targets.

(2) If, for example, the above-mentioned linearly polarized beam is used as a beam to be incident on a measurement target, phase difference information of ellipsometric parameters is obtained in the form of $\cos\Delta$. Therefore, it is impossible to determine whether a correct phase difference is $\Delta$ or $(360° - \Delta)$. In addition, if a circularly polarized beam is used as an incident beam, since phase difference information of ellipsometric parameters is obtained in the form of $\sin\Delta$, it is impossible to determine whether a correct phase difference is $\Delta$ or $(90° - \Delta)$.

It is, therefore, necessary to determine which quadrant (zone) of the first quadrant (0° to 90°) to the fourth quadrant (270° to 360°) the obtained phase difference $\Delta$ belongs to. This determination is generally called zone definition. In a general zone definition method, output waveforms are respectively obtained from a circularly polarized incident beam, which is formed by inserting a $\lambda/4$ plate in the optical path of a beam to be incident on a measurement target, and from a linearly polarized incident beam, which is formed without inserting a $\lambda/4$ plate in the optical path, and the two output waveforms are compared with each other to determine a zone to which the obtained phase difference belongs. However, in this method, since two measuring operations must be performed with respect to the same measurement point, the measurement efficiency is not necessarily increased much as compared with the above-described null ellipsometry.

(3) Although a beam reflected by a measurement target is elliptically polarized, the measurement precision is decreased as the elliptic shape approaches a circle. For this reason, a $\lambda/4$ plate needs to be inserted in the optical path of an incident or reflected beam to change the elliptical polarization state of a reflected beam to be incident on a measurement system. This further decreases the measurement efficiency.

(4) The conventional method requires a mechanism for rotating the analyzer and a mechanism for inserting/removing a $\lambda/4$ plate in/from an optical path. Since these mechanisms incorporate a large number of movable members, the apparatus itself is increased in size. Therefore, a place where the ellipsometer is installed is limited to a relatively large area with a good environment, e.g., a laboratory.

In addition, since the above-mentioned members are mechanically moved, a long period of time is required for moving operations. If the $\lambda/4$ plate is inserted/removed and the analyzer is rotated twice with respect to one measurement point, it takes a few seconds to perform a measurement with respect to one measurement point. Therefore, high-speed measurement in an on-line state cannot be performed.

The present invention has been made in consideration of the above situation, and has as its object to provide a measuring method for ellipsometric parameters and an ellipsometer, in which a reflected beam having an elliptically polarized beam, which is reflected by a measurement target, is divided into four different polarized light components, and the optical intensities of the respective polarized light components are detected to calculate ellipsometric parameters on the basis of the detected four optical intensities, so that the analyzer need not be rotated, the λ/4 plate need not be inserted/removed in/from an optical path, and only stationary members are required, thereby saving the time required to move movable members, allowing substantially instant measurement of ellipsometric parameters by one measuring operation, enabling on-line measurement of ellipsometric parameters with respect to moving measurement targets, and allowing measurement of film thicknesses.

SUMMARY OF THE INVENTION

In order to achieve the above object, according to the present invention, there is provided a measuring method for ellipsometric parameters, in which a polarized beam is radiated on a measurement target at a predetermined angle, a reflected beam from the measurement target is divided into four different polarized light components, and ellipsometric parameters are obtained o the basis of optical intensities of the four divided polarized light components.

In addition, according to a further aspect of the present invention, there is provided an ellipsometer comprising a light source section for radiating a polarized beam onto a measurement target at a predetermined angle, a non-polarizing beam splitter for splitting a beam reflected by the measurement target in two different directions, a plurality of optical parts for dividing each beam, split by the non-polarizing beam splitter, in two different polarization directions, and finally dividing the reflected beam, reflected by the measurement target, into four polarized light components, four light-receiving units for detecting optical intensities of the respective polarized light components divided by the plurality of optical parts, and an arithmetic section for calculating ellipsometric parameters of the elliptically polarized beam of the reflected beam on the basis of the four optical intensities detected by the four light-receiving units.

According to another aspect of the present invention, in the ellipsometer, the plurality of optical parts comprise two optical systems for dividing each beam split by the non-polarizing beam splitter into light components polarized in directions at +45° and −45° with respect to a reference direction, and a wave plate, inserted in at least one of optical paths of the beams split by the non-polarizing beam splitter and radiated on the respective optical systems, for changing a phase of a beam propagating through one optical path relative to a phase of a beam propagating through the other optical path.

According to still another aspect of the present invention, in the ellipsometer, the plurality of optical parts comprise a first optical system for dividing one beam, split by the non-polarizing beam splitter, into light components polarized in directions at +45° and −45° with respect to a reference direction, a second optical system for dividing the other beam, split by the non-polarizing beam splitter, into light components polarized at 90° and 0° with respect to the reference direction, and a wave plate, inserted in at least one of optical paths of the beams split by the non-polarizing beam splitter and radiated on the respective optical systems, for changing a phase of a beam propagating through one optical path relative to a phase of a beam propagating through the other optical path.

Furthermore, a wave plate can be inserted in an optical path of an incident or reflected beam to or from the measurement target.

According to still another aspect of the present invention, there is provided an ellipsometer comprising a light source section for radiating a polarized beam onto a measurement target at a predetermined angle, a composite beam splitter for splitting a beam reflected by the measurement target into four different polarized light components, four light-receiving units for detecting optical intensities of the polarized light components split by the composite beam splitter, and an arithmetic section for calculating ellipsometric parameters of an elliptically polarized beam of the reflected beam on the basis of the four optical intensities detected by the four light-receiving units.

According to still another aspect of the present invention, in the ellipsometer, the composite beam splitter comprises a non-polarizing glass for splitting the reflected beam from the measurement target, at an incident surface of the non-polarizing glass, into a reflected beam and a transmitted beam, a first polarizing beam splitter, having one end fixed to the non-polarizing beam glass, for splitting the reflected beam from the non-polarizing glass into light components polarized in directions which differ from each other by 90°, a second polarizing beam splitter, bonded to an exit surface of the non-polarizing glass, from which the transmitted beam emerges, for splitting the transmitted beam from the non-polarizing glass into light components polarized in directions which differ from each other by 90°, and a wave plate bonded to an incident surface of one of the first and second polarizing beam splitters.

DETAILED DESCRIPTION

The operation principle of the measuring method for ellipsometric parameters, will be described below. As described above, when a polarized beam from the light source section is incident on a measurement target at a predetermined angle $\phi$, a beam reflected by the measurement target has an elliptically polarized beam having a predetermined shape defined by the thickness or the like on the measurement target, as shown, e.g., in FIG. 3. The ellipsometric parameters $\Psi$ and $\Delta$ are the amplitude ratio $\Psi$ and the phase difference $\Delta$ between the P and S components of the reflected beam. Therefore, two ellipsometric parameters are required theoretically. If, for example, the incident beam is a linearly polarized beam, the sign of the phase difference $\Delta$ is determined depending on whether the elliptically polarized beam is polarized right-handed or left-handed. Since optical intensities measured by light-receiving units do not include data of the rotational direction of the elliptically polarized beam, another independent optical intensity data is required. If such three optical intensities can be obtained, no problem is posed. However, in order to perform a non-dimensional arithmetic operation independently of the absolute light amount, four optical intensities are required.

Figure 3A:
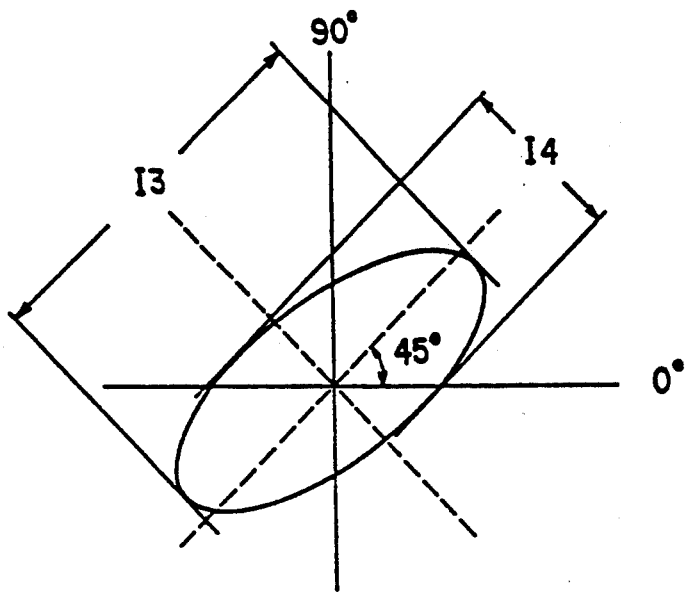
FIGS. 3(a) and 3(b) are views showing the elliptically polarized light components of a reflected beam in the ellipsometer of the embodiment of FIG. 1.
Figure 3B:
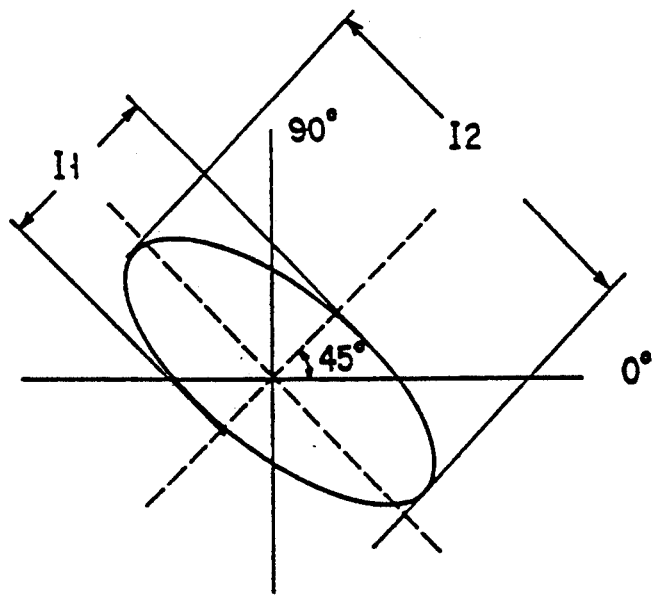

Therefore, if four optical intensities in total are obtained, i.e., two optical intensities obtaining by projecting the ellipse shown in FIG. 3(a) in the respective directions, and two optical intensities obtained by projecting the ellipse shown in FIG. 3(b), which is formed by giving a known phase difference to the ellipse in FIG. 3(a), in the respective directions, the ellipse is uniquely determined, including a specific quadrant to which the phase angle $\Delta$ belongs. For this reason, in the measuring method for ellipsometric parameters according to the present invention, a reflected beam from a measurement target is divided into four different polarized light components, and the ellipsometric parameters $\Psi$ and $\Delta$ are calculated on the basis of the optical intensities of the four divided light components.

Note that the polarization states of the beam shown in FIGS. 3(a) and 3(b) exhibit only relative states, and the present invention is not limited to these. Therefore, even if a different phase shift is given to the ellipse shown in FIG. 3(a) in advance, the present invention can be established as long as a known phase difference from the ellipse shown in FIG. 3(b) is defined.

In the ellipsometer of the present invention, a reflected beam having an elliptically polarized beam reflected by a measurement target is split in two directions by the non-polarizing beam splitter, and each split beam is further divided into light components polarized in two directions by a corresponding optical system. The wave plate is inserted in the optical path to one of the optical systems. With this arrangement, four different polarized light components are finally obtained and are converted into optical intensities. The ellipsometric parameters, i.e., the amplitude ratio $\Psi$ and the phase difference $\Delta$, are obtained by these four optical intensities.

In addition, each beam output from the non-polarizing beam splitter is set at angles of $+45°$ and $-45°$ with respect to a reference direction in which a direction (P component) parallel to the incident plane of the reflected beam from the measurement target is defined as an azimuth of $0°$, and the wave plate is inserted in one of the optical paths, thereby dividing the reflected beam into four different polarized light components.

By setting the polarization directions of each polarized light component at angles of $+45°$ and $-45°$ with respect to the reference direction using the wave plate, calculation of the ellipsometric parameters $\Psi$ and $\Delta$ can be simplified.

Furthermore, the reflected beam from the measurement target is divided into four different polarized light components by the composite beam splitter constituted by one optical part. By using the composite beam splitter, the number of optical parts can be reduced, and a compact, lightweight ellipsometer can be manufactured.

Moreover, the composite beam splitter is comprised of the non-polarizing glass, the first and second polarizing beam splitters, and the wave plate. In the composite beam splitter having such an arrangement, the reflected beam from the measurement target is divided into a transmitted beam and a reflected beam at the surface of the non-polarizing glass. The reflected beam is then divided into two polarized light components, which differ in polarization direction by $90°$, by the first polarizing beam splitter. Similarly, the transmitted beam is divided into two polarized light components, which differ in polarization direction by $90°$, by the second polarizing beam splitter. Since the wave plate is bonded to the incident surface of one of the polarizing beam splitters, the reflected beam is divided into four different polarized light components.

Embodiments of the present invention will be described below with reference to the accompanying drawings.

Figure 2:
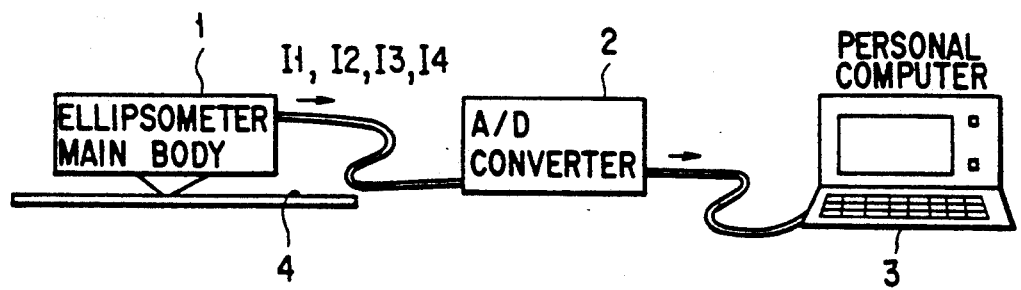
FIG. 2 is a view showing the overall arrangement of the ellipsometer of the embodiment of FIG. 1.

FIG. 2 is a block diagram showing the overall arrangement of an ellipsometer using a measuring method for ellipsometric parameters according to an embodiment of the invention. Referring to FIG. 2, reference numeral 1 denotes an ellipsometer main body housed in a case comprised of a light metal material. Optical intensities I1, I2, I3, and I4 output from the ellipsometer main body 1 are converted into digital values by an A/D converter 2. The digital values are then input to a personal computer 3 serving as an arithmetic section. The personal computer 3 calculates ellipsometric parameters $\Psi$ and $\Delta$ by using the input optical intensities I1, I2, I3, and I4. In addition, a film thickness d on a sample surface 4 as a measurement target is calculated on the basis of the calculated ellipsometric parameters $\Psi$ and $\Delta$ by using predetermined equations.

In this case, the A/D converter 2 sequentially A/D-converts the optical intensities I1, I2, I3, and I4 in a time-divisional manner. Note that a conversion time per optical intensity is about 10 $\mu$sec. Therefore, a measurement time required to measure the ellipsometric parameters $\Psi$ and $\Delta$ and the film thickness d at one measurement point sampled on the sample surface 4, including a calculation time in the personal computer 3, is about 100 $\mu$sec. Note that since the optical intensities I1, I2, I3, and I4 are simultaneously measured and held in a voltage holding circuit, even if the sample surface 4 moves at high speed, the above-described operation can be satisfactorily performed.

Figure 1:
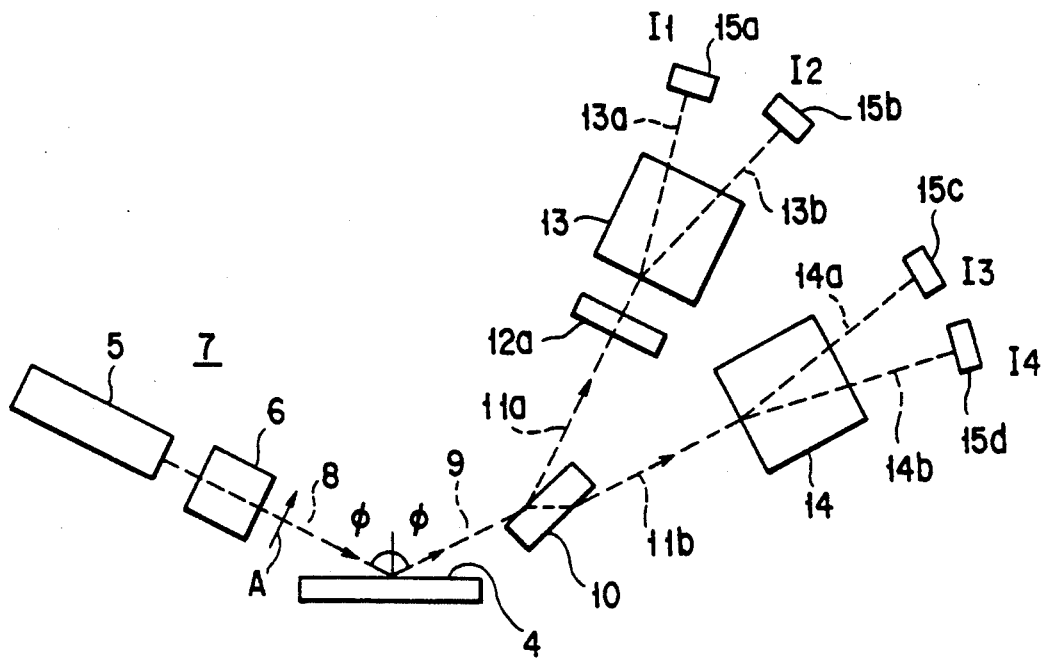
FIG. 1 is a view showing the internal structure of the main body of an ellipsometer according to an embodiment of the present invention.

FIG. 1 shows the internal arrangement of the ellipsometer main body 1. A laser beam having a single wavelength, which is emitted from a laser source 5, e.g., a semiconductor laser, is linearly polarized at an azimuth angle of $-45°$ with respect to a reference direction by a polarizer 6. That is, the laser source 5 and the polarizer 6 comprise a light source section 7. An incident beam 8, which is linearly polarized, is radiated from the light source section 7 onto the sample surface 4 at an angle $\phi$. Note that the reference direction is a direction in which a direction parallel to the incident plane of the incident beam 8 is defined as an azimuth of 0° when viewed from the sample surface 4, as indicated by an arrow A. In this case, the incident plane is a plane perpendicular to the sample surface 4 and including the incident beam 8 and a reflected beam 9.

The reflected beam 9 from the sample surface 4 is converted from the linearly polarized beam into an elliptically polarized beam shown in FIG. 3 because of the presence of a film on the sample surface 4. The elliptically polarized beam is then incident on a non-polarizing beam splitter 10.

The non-polarizing beam splitter 10 is comprises e.g., a non-polarizing glass plate. The incident beam 9, which is reflected from the sample surface, is split into two beams 11a and 11b while the beam 9 is not polarized at all and its elliptical polarization state is held. The reflected beam 11a is incident on a first polarizing beam splitter 13 through a $\lambda/4$ plate 12a. The transmitted beam 11b is directly incident on a second polarizing beam splitter 14.

The first and second polarizing beam splitters 13 and 14 have the same constitution. Each beam splitter comprises a Glan-Thompson prism, a Glan-Taylor prism, or the like and is designed to split an incident beam having an elliptically polarized beam into polarized light components in two orthogonal directions and to output them as transmitted and reflected beams, respectively. Note that each beam splitter may comprise a Wollaston prism or the like designed to split a transmitted beam into two components at a certain angle.

The first polarizing beam splitter 13 is positioned such that a transmitted beam 13a from the first polarizing beam splitter 13 is polarized counterclockwise at an angle of $+45°$ with respect to the above-mentioned reference direction in which the direction parallel to the incident plane is defined as an azimuth of 0°, when viewed from the direction of a light-receiving unit 15a. The transmitted beam 13a output from the first polarizing beam splitter 13 and polarized at an angle 45° is incident on the light-receiving unit 15a. The light-receiving unit 15a outputs a signal corresponding to the optical intensity I1 of the received polarized light component. A reflected beam 13b output from the first polarizing beam splitter 13 and polarized at an azimuth angle of $-45°$ is incident on a light-receiving unit 15b to be converted into the optical intensity I2.

The second polarizing beam splitter 14 is positioned such that a transmitted beam 14a from the second polarizing beam splitter 14 is polarized at an azimuth angle of $+45°$ with respect to the reference direction. The transmitted beam 14a output from the second polarizing beam splitter 14 and polarized at an azimuth angle of $+45°$ is incident on a light-receiving unit 15c to be converted into the optical intensity I3. A reflected beam 14b output from the second polarizing beam splitter 14 and polarized at an azimuth angle of $-45°$ is incident on a light-receiving unit 15d to be converted into the optical intensity I4.

Since the $\lambda/4$ plate 12a is inserted in the optical path of the reflected beam 11a to be incident on the first polarizing beam splitter 13, the phase difference between the P- and S-polarized light components of the reflected beam 11a which is elliptically polarized and incident on the first polarizing beam splitter 13 is changed by 90°. Therefore, the polarized light components which are respectively incident on the light-receiving units 15a to 15d have different values. More specifically, the polarized light components of the elliptically polarized beam of the reflected beam 9, which are respectively obtained by the light-receiving units 15a to 15d, include both $\cos\Delta$ information and $\sin\Delta$ information.

As described above, the ellipsometric parameters $\Psi$ and $\Delta$, which specify the elliptically polarized beam shown in FIG. 3, are calculated by using the four optical intensities I1 to I4.

$$\tan\Delta = \{[\sigma_R(I1 - I2)]1/[\sigma_T(I3 - I4)]\} \quad (2)$$

$$\tan\psi = [(\sigma_R^2 - \sigma_T^2)/2] \times \{\{\sigma_R(I1 - I2)\}^2 + \{\sigma_T(I3 - I4)\}^2\}^{\frac{1}{2}} \div [\sigma_R^2(I1 + I2) - \sigma_T^2(I3 + I4)] \quad (3)$$

Note that an amplitude reflectance ratio $\sigma_R$ and an amplitude transmittance ratio $\sigma_T$ between the p- and S-polarized light components from the non-polarizing beam splitter 10 are inherent values. A test beam having a known linearly or elliptically polarized beam is radiated on the non-polarizing beam splitter 10, and these inherent values are obtained in advance on the basis of deviations from the true ellipsometric parameters $\Psi$ and $\Delta$.

In addition, when the phase difference $\Delta$ is to be calculated, a quadrant (zone) is determined depending on whether the following values $\sigma R(I1 - I2)$ and $\sigma T(I3 - I4)$ are negative or positive.

More specifically, let $\sigma R(I1 - I2)$ be A and $\sigma T(I3 - I4)$ be B, then zone determination is performed as follows:

---
(1) If A > 0 and B > 0, the first quadrant
    (0° < $\Delta$ < 90°) is determined.
(2) If A > 0 and B < 0, the second quadrant
    (90° < $\Delta$ < 180°) is determined.
(3) If A < 0 and B < 0, the third quadrant
    (180° < $\Delta$ < 270°) is determined.
(4) If A < 0 and B > 0, the fourth quadrant
    (270° < $\Delta$ < 360°) is determined.
---

Therefore, a specific quadrant of the first to fourth quadrants, to which the calculated phase difference $\Delta$ belongs, can be simultaneously determined. As a result, it can be accurately determined whether the true value of the obtained phase difference $\Delta$ is $\Delta$ or $(360°-\Delta)$, $(90°-\Delta)$, or the like.

When ellipsometric parameters, i.e., the amplitude ratio $\Psi$ and the phase difference $\Delta$ including the quadrant to which it belongs, are obtained, the film thickness d on the sample surface 4 is calculated by using another equation.

In the ellipsometer having the above-described arrangement, the ellipsometric parameters $\Psi$ and $\Delta$ are almost instantly calculated by the personal computer 3, on the basis of the four optical intensities I1, I2, I3, and I4 simultaneously detected by the light-receiving units 15a, 15b, 15c, and 15d, according to equations (2) and (3). Subsequently, the film thickness d on the sample surface 4 is almost instantly calculated.

Even if, therefore, a measurement target moves at high speed, the film thickness d at a designated measurement point can be measured. That is, if the ellipsometric parameters $\Psi$ and $\Delta$ and the film thickness d are calculated by reading the respective optical intensities I1 to I4 at a predetermined period while the incident beam 8 is emitted from the light source section 7 and a measurement target is moved at a constant speed, the film thickness d on the surface of a belt-like product which continuously moves on, e.g., an inspection line in a factory can be continuously measured in an on-line manner.

In addition, as shown in FIG. 1, since the beam which is elliptically polarized and reflected by the sample surface 4 is divided into four different polarized light components, and the optical intensities I1 to I4 of the polarized light components are read at the same time, the ellipsometer of this embodiment does not require mechanism for rotating an analyzer and inserting-/removing a $\lambda/4$ plate so as to obtain polarized light components with different conditions as in the conventional ellipsometer. For this reason, all the optical parts can be constituted by only stationary members and no movable members are required, thus allowing a reduction in size and weight of the ellipsometer as a whole. This allows installation of the ellipsometer in a narrow place, e.g., a production site in a factory and hence widens the application range of the ellipsometer.

Furthermore, the phase difference $\Delta$ can be accurately calculated regardless of the range of its values. In the conventional apparatus, for example, if the incident beam on the sample surface 4 is a linearly polarized beam, measurement precision is very poor at a place where the phase difference $\Delta$ is around 90° or 270°, as compared with other places. However, in the ellipsometer of the present invention, accurate measurement can be performed even at a place where the phase difference $\Delta$ is around 90° or 270°.

In order to prove this, in the ellipsometer shown in FIG. 1, the present inventors radiated an incident beam 8 onto the sample surface 4 having various known film thicknesses d to form reflected beams 9 having elliptically polarized beams of various shapes, and measured the ellipsometric parameters of the respective elliptically polarized beams. In this experiment, with respect to the respective phase differences $\Delta$ from 0° to 360°, measurement errors were able to be limited to a maximum of 5% and an average of 3%. In addition, a measurement error of the amplitude ratio $\Psi$ was about 5%.

Figure 4:
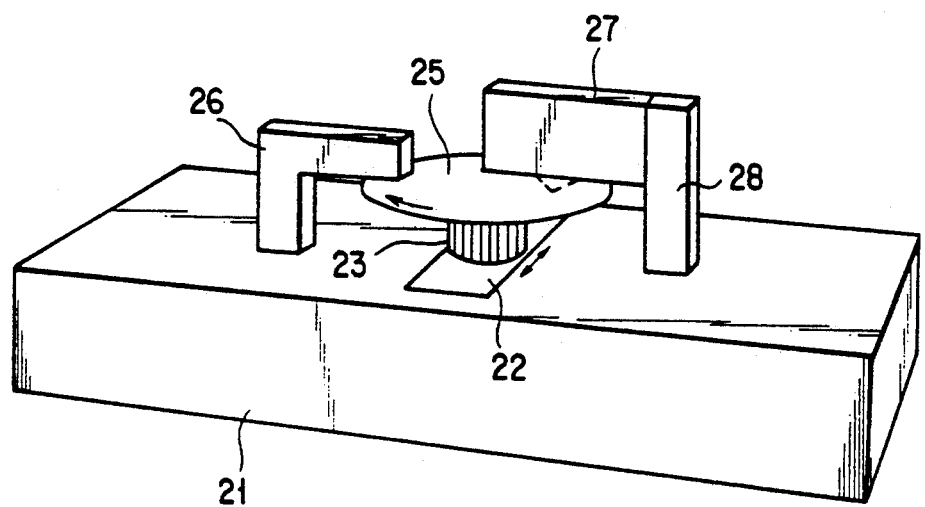
FIG. 4 is a schematic view showing the arrangement of an apparatus for measuring the thickness of an oxide film on a silicon wafer, which uses the ellipsometer of the present invention.

FIG. 4 shows a state wherein the ellipsometer of the embodiment is incorporated in an apparatus for measuring the distribution of oxide film thickness on a silicon wafer.

A moving table 22 is arranged on a base 21. A rotating support base 23 is mounted on the moving table 22. A silicon wafer 25 as a measurement target is attached to the rotating support base 23 by e.g., a suction mechanism. With this arrangement, the silicon wafer 25 is rotated and linearly moved in directions indicated by arrows in FIG. 4. A known thickness measuring unit 26 for measuring the overall thickness of the silicon wafer 25 is arranged on the base 21. In addition, an ellipsometer main body 27 is fixed on the base 21 by a support member 28 to oppose the thickness measuring unit 26.

The thickness measuring unit 26 and the ellipsometer main body 27 respectively measure the overall thickness of the silicon wafer 25 and the thickness d of the oxide film at each measurement position of the silicon wafer, which is spirally moved by the moving table 22 and the rotating support base 23. In addition, the position of the moving table 22 and the rotational angle of the silicon wafer 25 are controlled by a computer incorporated in the apparatus. Therefore, measurement positions and measurement results have one-to-one correspondence, and such correspondence can be visually comprehended at once on the display screen of, e.g., a CRT display unit.

In order to confirm the effects of the apparatus of the embodiment, the apparatus of the embodiment shown in FIG. 4 was compared with the conventional apparatus using the rotating analyzer. An optical system was used to cause a linearly polarized beam as an incident beam to be incident onto a measurement target at an incident angle of 62°. In addition, a silicon wafer 25 on which a nitride film having a refractive index of 1.65 and a thickness d=800 nm was formed was used as a measurement target.

In this case, since the film thickness d is 800 nm, the phase difference $\Delta$ as an ellipsometric parameter at a portion where the nitride film is formed is theoretically 94.1°, whereas the phase difference $\Delta$ at a portion where no nitride film is formed is 0°.

For this reason, when measurement is to be performed by the conventional apparatus using the rotating analyzer, a circularly polarized beam must be used as an incident beam with respect to a portion where the nitride film is formed, and a linearly polarized beam must be used as an incident beam with respect to a portion where no nitride film is formed. Therefore, when the silicon wafer 25 having such conditions is to be measured, for example, a λ/4 plate must be inserted to measure a portion where the nitride film is formed, and the λ/4 plate must be removed to measure a portion where no nitride film is formed. Therefore, at each measurement point on the silicon wafer 25, two measuring operations must be performed, i.e., measurement in a state wherein the λ/4 plate is inserted and in a state wherein the λ/4 plate is removed. In the experiment, it took about five hours to measure thicknesses at about 5,000 points, at intervals of 2 mm, on the entire surface of the silicon wafer 25 having a diameter of 6 inches. In practice, therefore, the conventional apparatus cannot be used on a production inspection line of silicon wafers.

In contrast to this, in the apparatus of the embodiment of the present invention in which four optical intensities are simultaneously measured, a time required for measurement per point, including a time required to move a measurement point, is about 2 msec, and a time required to measure the same silicon wafer 25 is about 10 sec. Therefore, the apparatus of the embodiment of the present invention has a processing speed high enough to be incorporated in an actual production inspection line.

As described above, since the processing speed of the ellipsometer is increased while its size is reduced, the ellipsometer can be additionally installed with respect to the known thickness measuring unit 26. With regard to a semiconductor process line, the ellipsometer of the embodiment can be applied to on-line measurement of nitride films, polysilicon films, transparent electrode members, and the like other than the above-mentioned silicon wafers.

Figure 5:
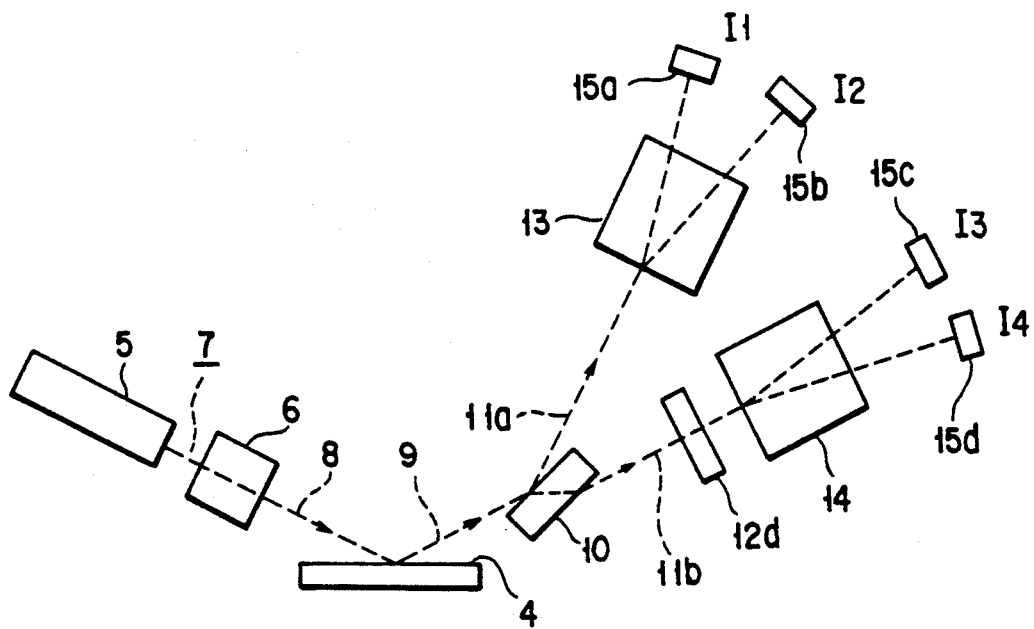
FIG. 5 is a view showing the structure of another embodiment of the present invention in which a wave plate is arranged in the other optical path unlike a wave plate in the embodiment shown in FIG. 1.

FIG. 5 shows the schematic arrangement of an ellipsometer according to another embodiment of the present invention.

The same reference numerals in FIG. 5 denote the same parts as in FIG. 1, and hence a repetitive description will be avoided. In this embodiment, a λ/4 plate 12b is inserted in the optical path of a transmitted beam 11b from a non-polarizing beam splitter 10, which is incident on a second polarizing beam splitter 14. The λ/4 plate 12a in FIG. 1 is omitted.

In the ellipsometer having the above-described arrangement, the phase difference between the P- and S-polarized light components of the transmitted beam 11b incident on the second polarizing beam splitter 14 is changed by 90°. Consequently, four different polarized light components are respectively incident on light-receiving units 15a to 15d. Therefore, the same operation as that in the embodiment shown in FIG. 1 can be performed.

Figure 6:
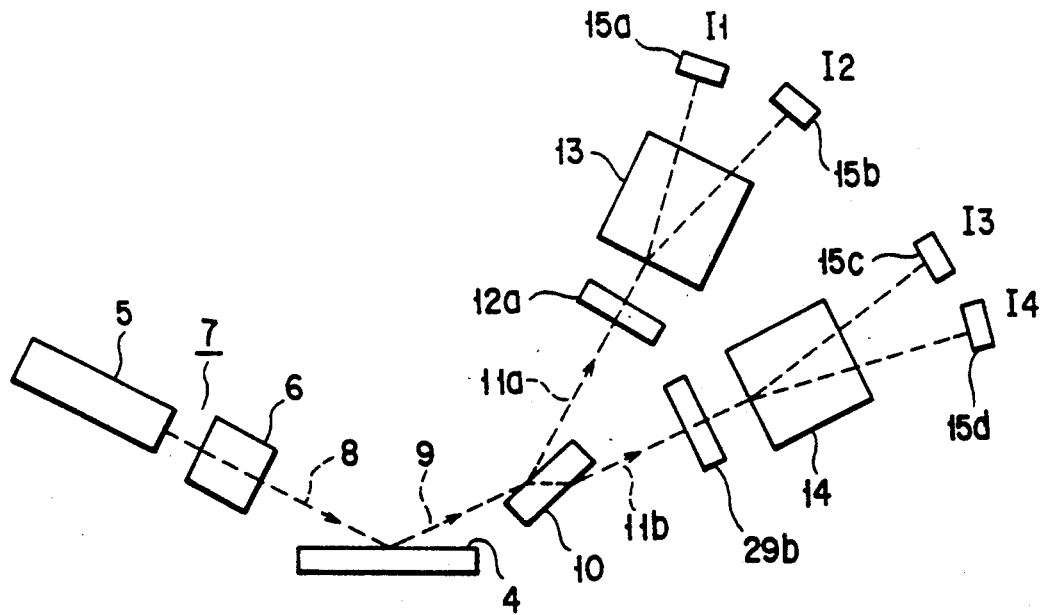
FIG. 6 is a view showing the structure of still another embodiment using two wave plates.

In the ellipsometer shown in FIG. 6, a λ/4 plate 12a identical to the one in FIG. 1 is inserted in the optical path of a beam incident on a first polarizing beam splitter 13, and a λ/2 plate 29b is inserted in the optical path of a beam incident on a second polarizing beam splitter 14. Even in such an arrangement, since the P- and S-polarized light components of elliptically polarized beams incident on the polarizing beam splitters 13 and 14 differ in phase by 90°, four light components polarized in different directions are respectively incident on light-receiving units 15a to 15d. Therefore, substantially the same effects as those in the above-described embodiments can be obtained.

Figure 7:
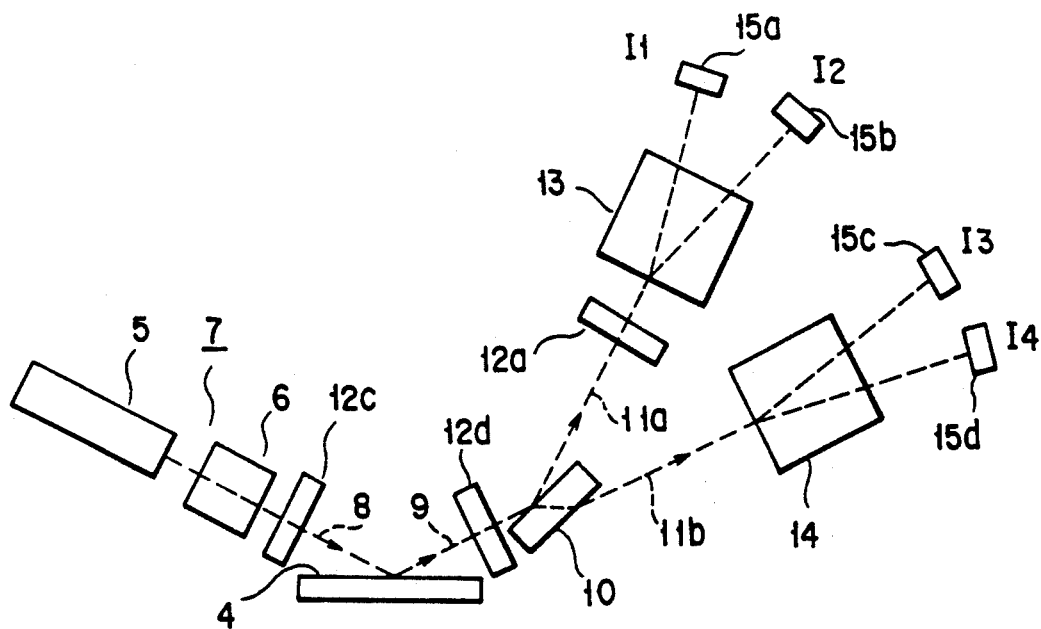
FIG. 7 is a view showing the structure of still another embodiment in which wave plates are respectively inserted in the optical paths of incident/ reflected beams to/from a sample surface.
Figure 8:
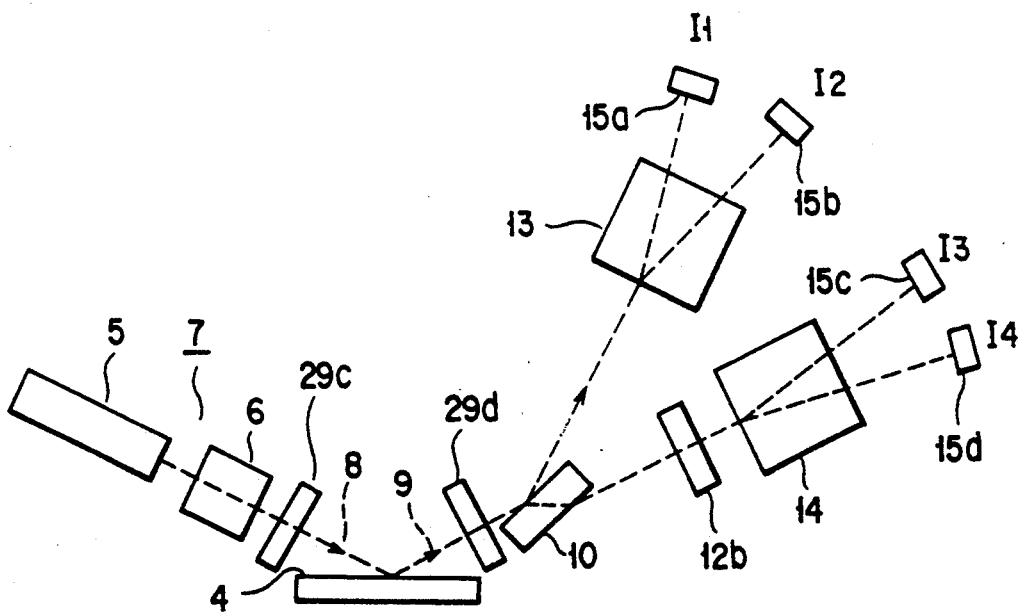
FIG. 8 is a view showing the structure of still another embodiment in which a wave plate is inserted in only the optical path of a reflected beam from the sample surface.
Figure 9:
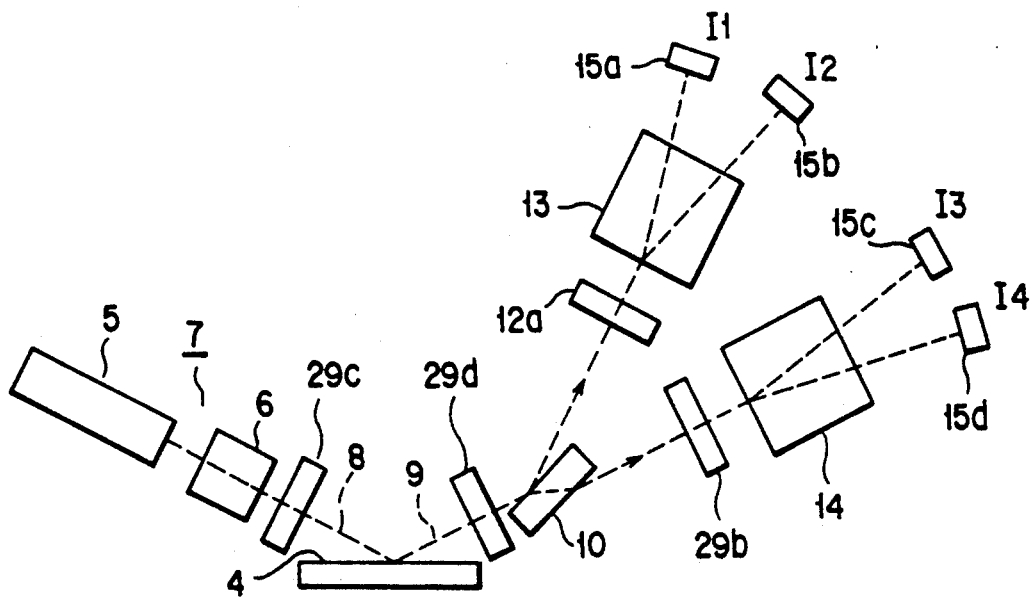
FIG. 9 is a view showing the structure of still another embodiment in which a wave plate is inserted in only the optical path of a reflected beam from the sample surface.

FIGS. 7, 8, and 9 show embodiments in which λ/4 plates 12c and 12d or λ/2 plates 29c and 29d are respectively inserted in the optical paths of the incident beam 8 and the reflected beam 9 with respect to the sample surface 4 in the ellipsometers shown in FIGS. 1, 5, and 6. By inserting wave plates in the optical paths of incident and reflected beams to/from the sample surface 4 in this manner, the phase difference between the P- and S-polarized light components of the incident beam 8 can be arbitrarily changed.

Figure 10:
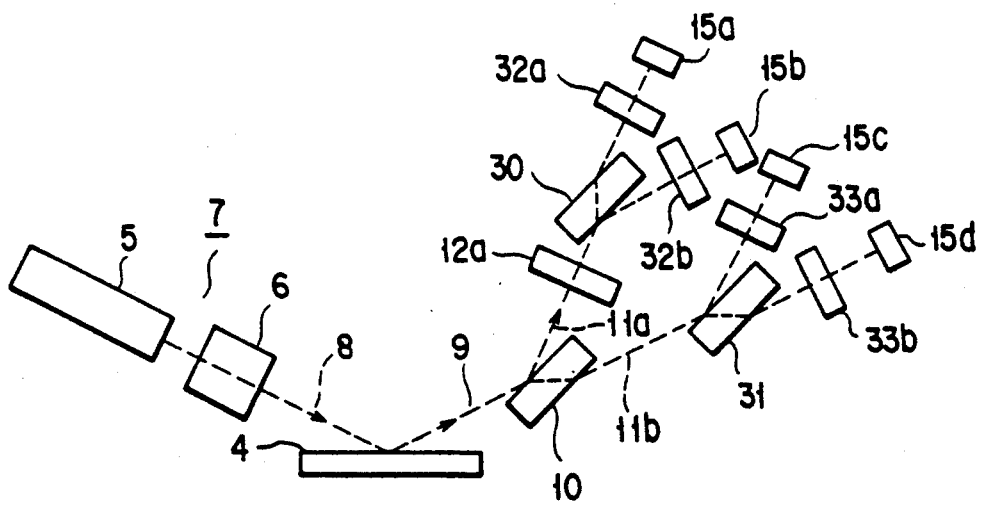
FIG. 10 is a view showing the structure of still another embodiment using analyzers.
Figure 11:
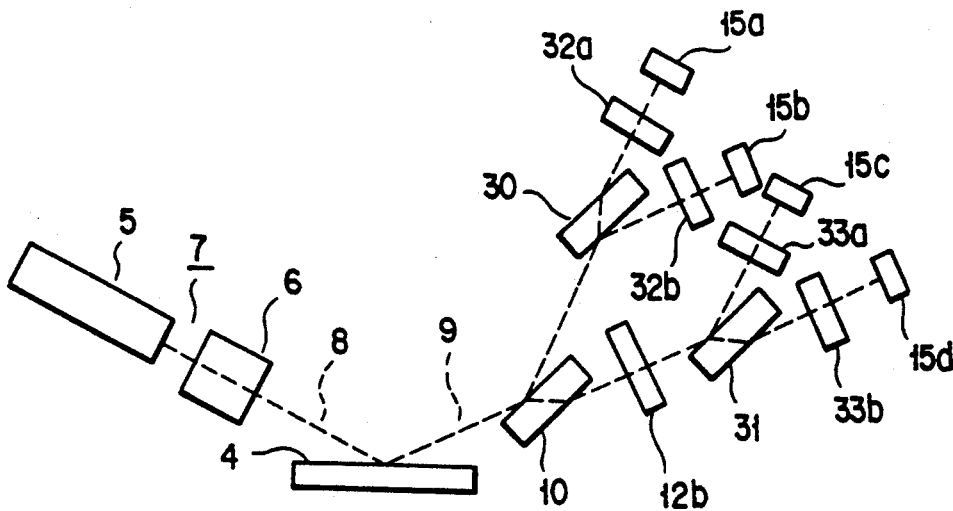
FIG. 11 is a view showing the structure of still another embodiment of the present invention using analyzers.
Figure 12:
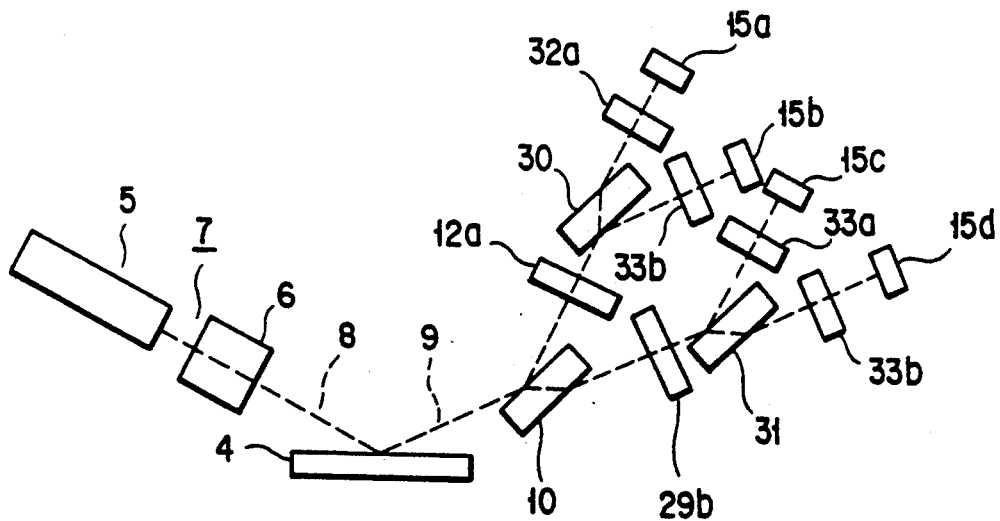
FIG. 12 is a view showing the structure of still another embodiment using analyzers.
Figure 13:
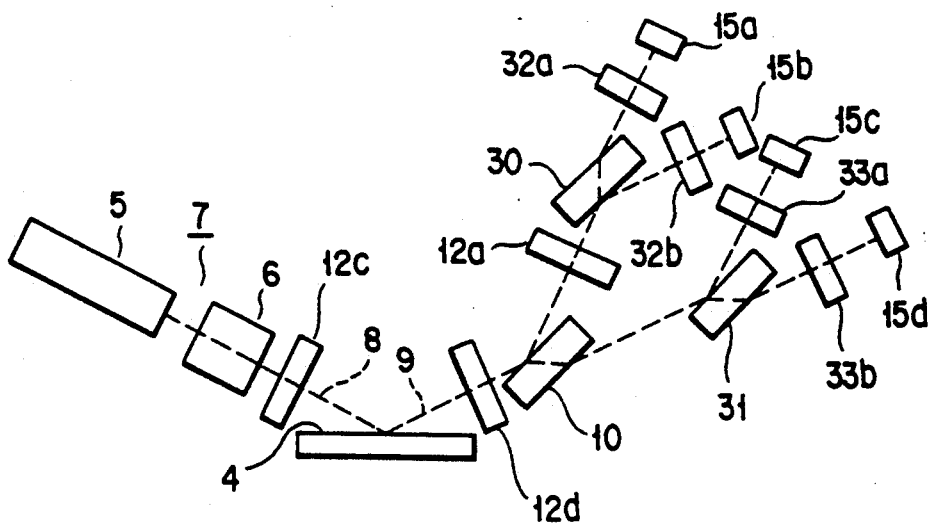
FIG. 13 is a view showing the structure of still another embodiment using analyzers.
Figure 14:
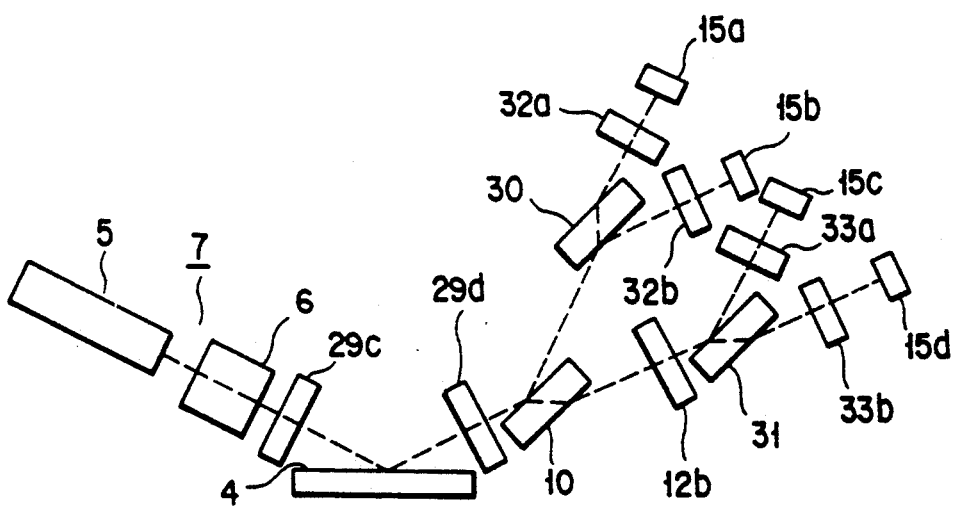
FIG. 14 is a view showing the structure of still another embodiment using analyzers.
Figure 15:
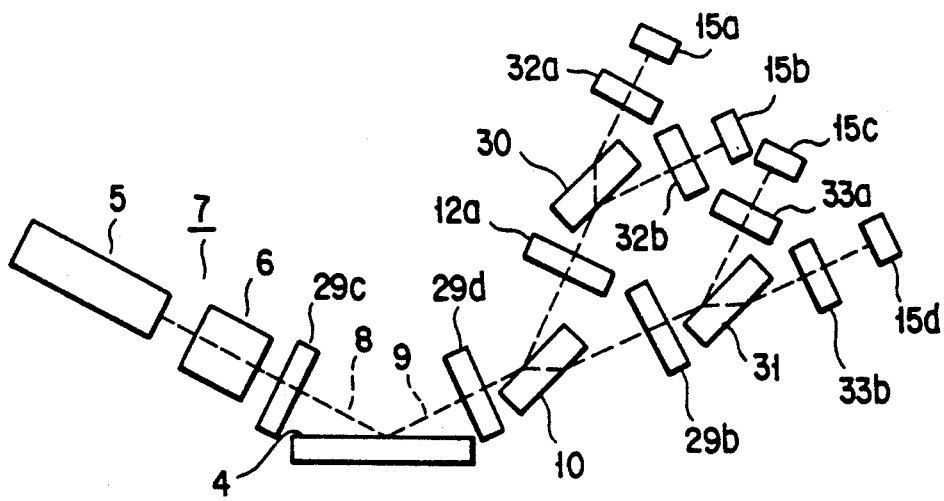
FIG. 15 is a view showing the structure of still another embodiment using analyzers.

Referring to FIG. 10, non-polarizing beam splitters and analyzers are used as two optical systems for extracting different polarized light components of a reflected beam 11a and a transmitted beam 11b from a non-polarizing beam splitter 10.

More specifically, the ellipsometer of FIG. 10 includes a first non-polarizing beam splitter 30 on which the reflected beam 11a is incident through a λ/4 plate 12a, an analyzer 32a for extracting a light component, of the reflected beam from the first non-polarizing beam splitter 30, which is polarized in a direction at +45° with respect to the reference direction, and an analyzer 32b for extracting a light component, of the transmitted beam from the first non-polarizing beam splitter 30, which is polarized in a direction at −45°.

The ellipsometer of FIG. 10 further includes a second non-polarizing beam splitter 31 on which the transmitted beam 11b is directly incident, an analyzer 33b for extracting a light component, of the reflected beam from the second non-polarizing plate 31, which is polarized in a direction at +45° with respect to the reference direction, and an analyzer 33b for extracting a light component, of the transmitted beam from the second non-polarizing beam splitter 31, which is polarized at in a direction at −45° with respect to the reference direction.

Even if optical systems formed by combining non-polarizing beam splitters and analyzers are used in this manner in place of polarizing beam splitters, basically the same effects as those of the embodiment shown in FIG. 1 can be obtained, although the equations for calculating the ellipsometric parameters $\Psi$ and $\Delta$ must be slightly modified because the optical systems are slightly complicated.

FIGS. 11, 12, 13, 14, and 15 show ellipsometers in which the polarizing beam splitters 13 and 14 of the ellipsometers of the embodiments shown in FIGS. 5, 6, 7, 8, and 9 are respectively replaced with the non-polarizing beam splitters 30 and 31 and the analyzers 32a, 32b, 33a, and 33b described with reference to the embodiment shown in FIG. 10. Therefore, substantially the same effects as those of the embodiments respectively shown in FIGS. 5 to 9 can be obtained.

Figure 16:
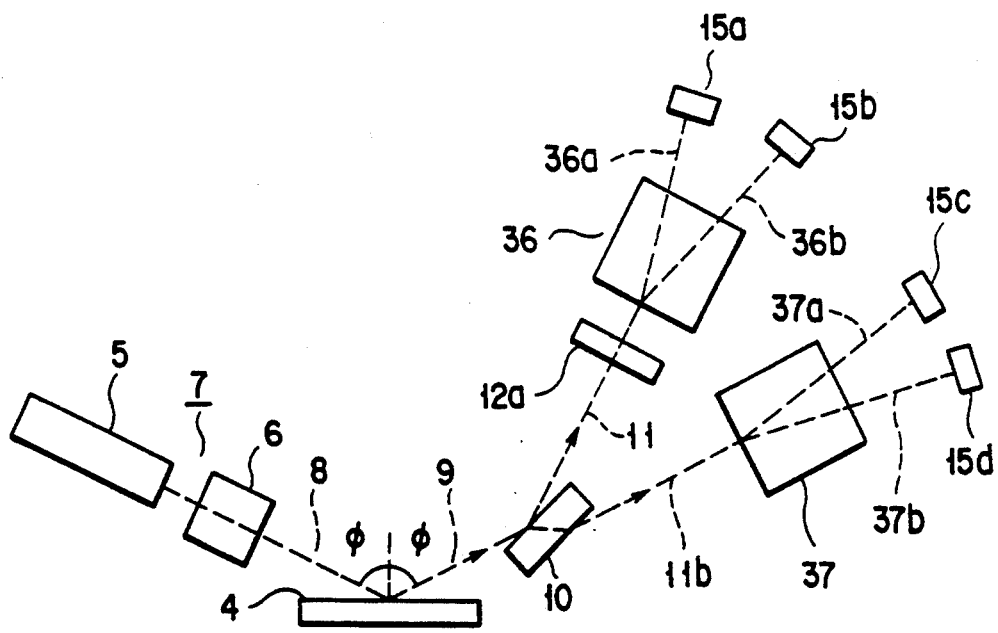
FIG. 16 is a view showing the structure of still another embodiment using polarizing beam splitters set in different polarization directions.
Figure 17:
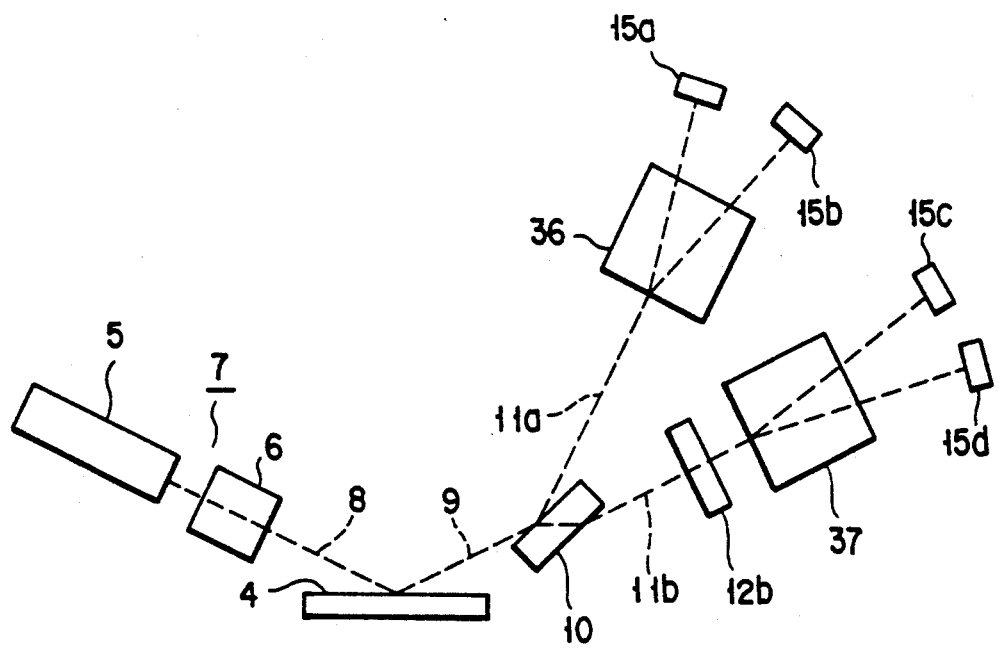
FIG. 17 is a view showing the structure of still another embodiment using polarizing beam splitters set in different polarization directions.
Figure 18:
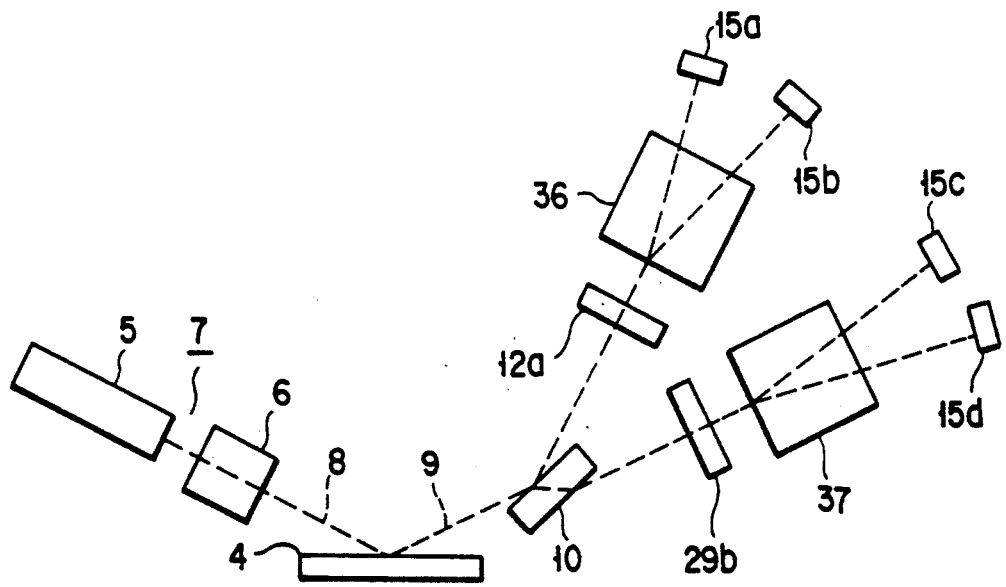
FIG. 18 is a view showing the structure of still another embodiment using polarizing beam splitters set in different polarization directions.
Figure 19:
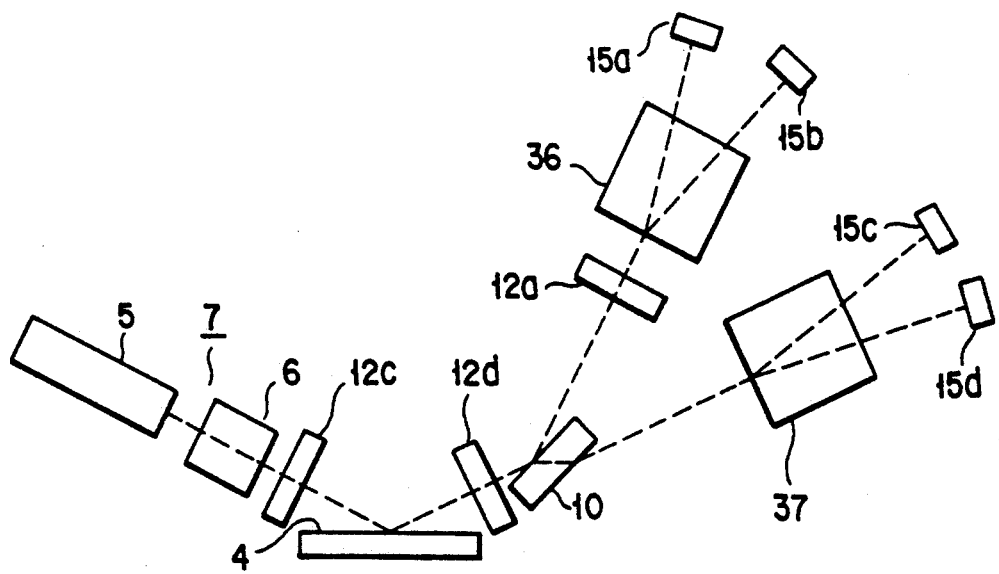
FIG. 19 is a view showing the structure of still another embodiment using polarizing beam splitters set in different polarization directions.
Figure 20:
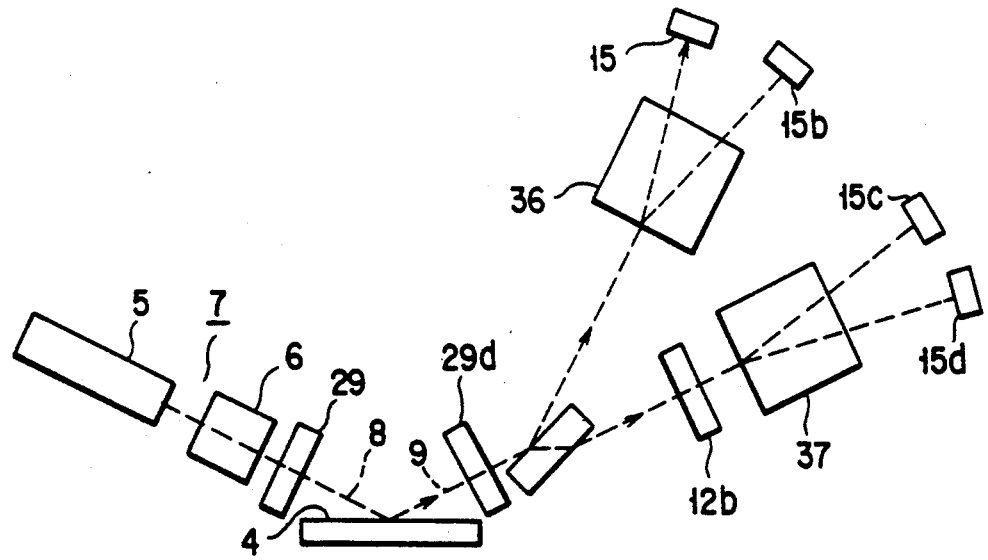
FIG. 20 is a view showing the structure of still another embodiment using polarizing beam splitters set in different polarization directions.
Figure 21:
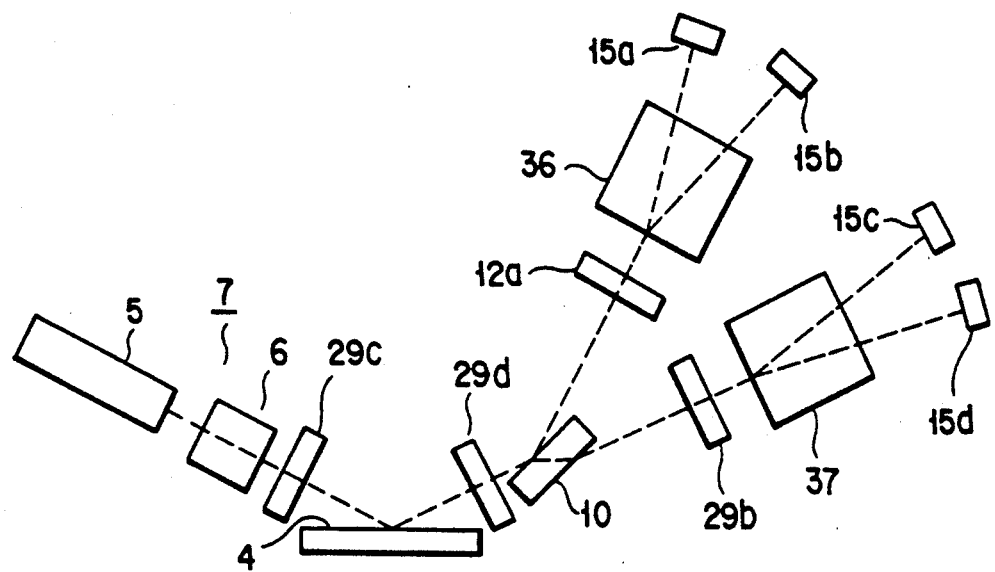
FIG. 21 is a view showing the structure of still another embodiment using polarizing beam splitters set in different polarization directions.

FIG. 16 shows the schematic arrangement of an ellipsometer according to still another embodiment of the present invention. The same reference numerals in FIG. 16 denote the same parts as in FIG. 1, and a repetitive description will be avoided.

In the embodiment of FIG. 16, the position of a first polarizing beam splitter 36 is fixed such that a transmitted beam 36a output from the first polarizing beam splitter 36 is polarized in a direction at 90° with respect to the above-mentioned reference direction. The position of a second polarizing beam splitter 37 is fixed such that a transmitted beam 37a output from the second polarizing beam splitter 37 is polarized in a direction at +45° with respect to the reference direction. Consequently, a reflected beam 36b from the first polarizing beam splitter 36 is polarized in a direction at +0° with respect to the reference direction, and a reflected beam 37b from the second polarizing beam splitter 37 is polarized in a direction at −45° with respect to the reference direction. In addition, a λ/4 plate 12a is arranged to be inclined in a direction at 45° with respect to the reference direction.

With this arrangement, ellipsometric parameters Ψ and Δ are calculated by using optical intensities I1 to I4 obtained by light-receiving units 15a to 15d. Therefore, substantially the same effects as those of the embodiment shown in FIG. 1 can be obtained.

FIGS. 17, 18, 19, 20, and 21 show ellipsometers in which the positions of the polarizing beam splitters 13 and 14 in the embodiments shown in FIGS. 5, 6, 7, 8, and 9 are set as follows. As shown in FIG. 16, in each embodiment, one beam splitter having a λ/4 plate inserted in its optical path is positioned such that the polarization directions are set at angles of 0° and 90° with respect to the reference direction. The other beam splitter is positioned such that the polarization directions are set at angles of +45° and −45° with respect to the reference direction. Therefore, substantially the same effects as those of the embodiments shown in FIGS. 5 to 9 can be obtained.

Figure 22:
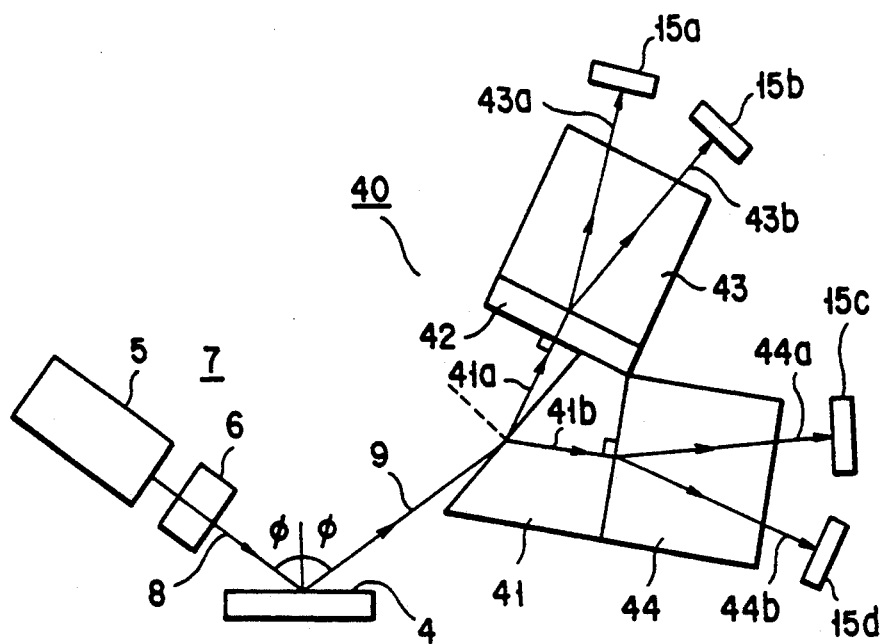
FIG. 22 is a view showing the structure of still another embodiment using a composite beam splitter.

FIG. 22 shows the schematic arrangement of an ellipsometer according to still another embodiment of the present invention. The same reference numerals in FIG. 22 denote the same parts as in FIG. 1, and a repetitive description will be avoided.

In the embodiment of FIG. 22, a reflected beam 9 having an elliptically polarized light component from a sample surface 4 is incident on a composite beam splitter 40. The composite beam splitter 40 comprises a non-polarizing glass member 41 having a four-cornered sectional shape, a first polarizing beam splitter 43, and a second beam splitter 44. Part of the incident surface of the first polarizing beam splitter 43 is fixed to the upper surface of the non-polarizing glass member 41 with, e.g., an adhesive agent. A λ/4 plate 42 is bonded to the incident surface. The incident surface of the second polarizing beam splitter 44 is bonded to the exit surface of the non-polarizing glass member 41.

The reflected beam 9 from the sample surface is divided into a reflected beam 41a and a transmitted beam 41b by the incident surface of the non-polarizing glass member 41 while its elliptical polarization state is maintained. The reflected beam 41a from the non-polarizing glass member 41 is perpendicularly 41b is transmitted through the non-polarizing glass member 41 to be perpendicularly incident on the incident surface of the second polarizing beam splitter 44. That is, the installation angle of the composite beam splitter 40 with respect to the reflected beam 9, and the angle of the incident surface of the non-polarizing glass member 41 are adjusted such that the reflected beam 41a and the transmitted beam 41b are perpendicularly incident on the incident surfaces of the first and second polarizing beam splitters 43 and 44, respectively.

The first polarizing beam splitter 43 splits the reflected beam 41a received through the λ/4 plate 42 into a transmitted beam 43a having a light component polarized in a direction at 45° with respect to the above-mentioned reference direction, and a reflected beam 43b having a light component polarized in a direction at −45° with respect to the reference direction. Similarly, the second polarizing beam splitter 44 splits the transmitted beam 41b, which is transmitted through the non-polarizing glass 41, into a transmitted beam 44a having a light component polarized in a direction at 45° with respect to the reference direction, and a reflected beam 44b having a light component polarized in a direction at −45° with respect to the reference direction, and causes them to be incident on light-receiving units 15c and 15d, respectively.

In this ellipsometer, since the λ/4 plate 42 is inserted in the optical path of the reflected beam 41a incident on the first polarizing beam splitter 43, the phase difference between the P- and S-polarized light components of the reflected beam 41a which is elliptically polarized and incident on the first polarizing beam splitter 43 is changed by 90°. As a result, polarized light components incident on the respective light-receiving units 15a to 15d have different values. That is, optical intensities obtained by the light-receiving units 15a to 15d contain information of tanΨ, cosΔ, and sinΔ. By using optical intensities I1 to I4 obtained by the light-receiving units 15a to 15d, ellipsometric parameters Ψ and Δ, which specify the elliptically polarized beam shown in FIG. 3, are calculated in the same manner as in the embodiment shown in FIG. 1. Therefore, substantially the same effects as those of the embodiment in FIG. 1 can be obtained.

Furthermore, in this embodiment, a plurality of optical elements for dividing the reflected beam 9, reflected by the sample surface 4, into four different polarized light components are bonded to each other with, e.g., an adhesive agent to comprise one optical part. Therefore, in the manufacture of this ellipsometer, assembly and adjustment can be greatly simplified. In addition, since the number of parts is small, inspection and maintenance operations can be simplified over a long-term operation period. Moreover, the overall apparatus can be reduced in size and weight.

Figure 23:
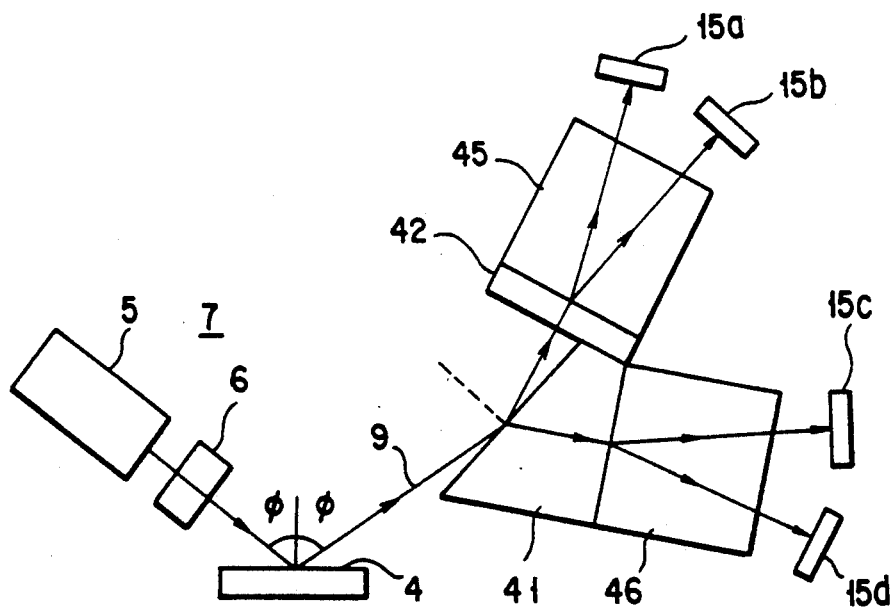
FIG. 23 is a view showing the structure of still another embodiment using a composite beam splitter.

FIG. 23 shows an embodiment in which the installation angle of each polarizing beam splitter in a direction around the optical axis is changed to change the polarization direction of a polarized light component extracted from each polarizing beam splitter, in the embodiment shown in FIG. 22.

That is, in the embodiment of FIG. 23, the polarization directions of polarized light components extracted from a first polarizing beam splitter 45 are set at angles of 90° and 0° with respect to the reference direction.

In the ellipsometer having the above-described arrangement, since optical intensities I1 to I4 of beams polarized in different directions can be obtained, substantially the same effects as those of the embodiment shown in FIG. 22 can be obtained.

Figure 24:
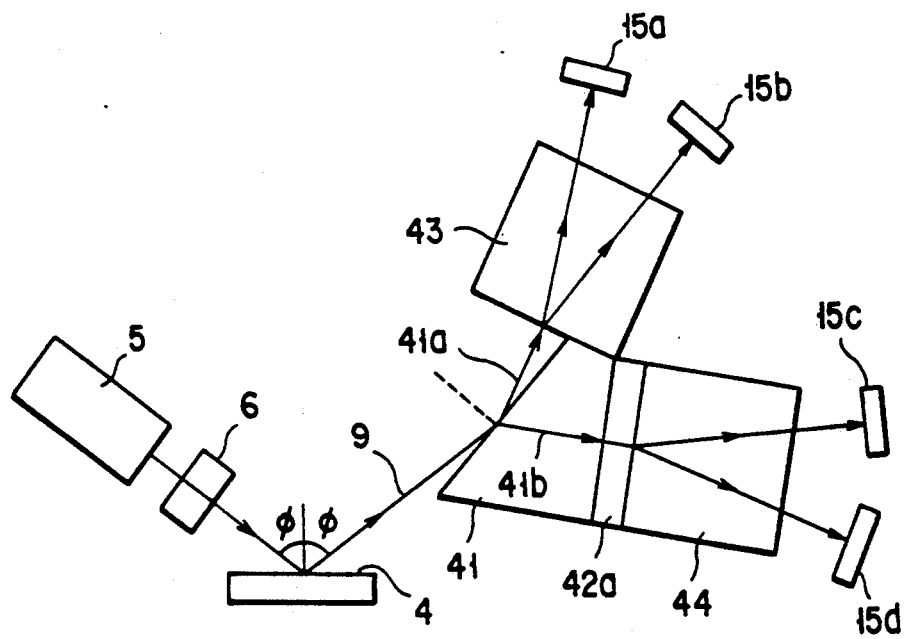
FIG. 24 is a view showing the structure of still another embodiment using a composite beam splitter.

FIG. 24 shows an embodiment in which the λ/4 plate 42 in the embodiment in FIG. 22 is moved to the incident surface of a second polarizing beam splitter 44.

In the embodiment of FIG. 24, a transmitted beam 41b from a non-polarizing glass member 41 is incident on the second polarizing beam splitter 44 through a λ/4 plate 42a to extract light components polarized in directions at 45° and −45°. Since optical intensities I1 to I4 based on beams polarized in different directions are obtained by light-receiving units 15a to 15d, substantially the same effects as those of the embodiment shown in FIG. 22 can be obtained.

Figure 25:
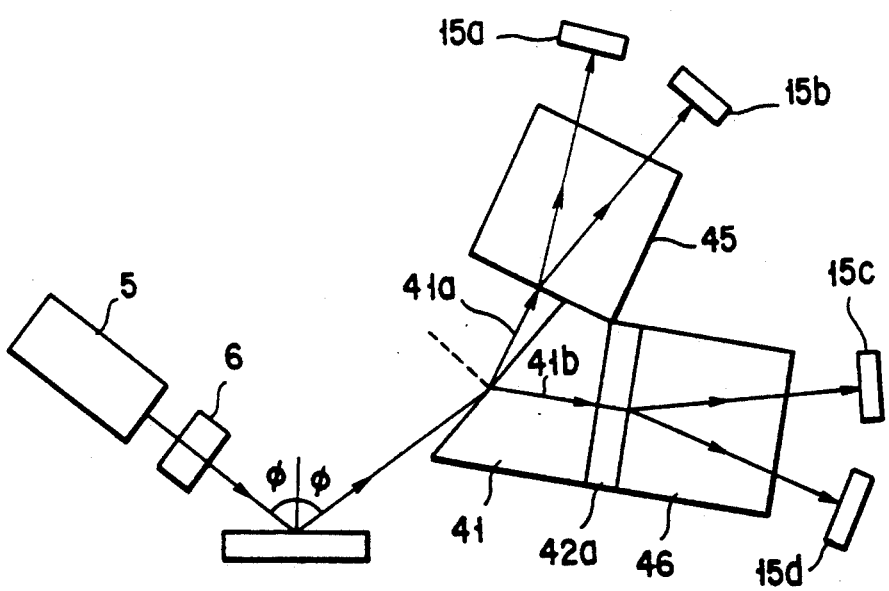
FIG. 25 is a view showing the structure of still another embodiment using a composite beam splitter.

FIG. 25 shows an embodiment in which the λ/4 plate 42 in the embodiment in FIG. 23 is moved to the incident surface of a second polarizing beam splitter 46. At the same time, the detection directions in a first polarizing beam splitter 45 are changed to directions at +45° and −45°, and the detection directions in the second polarizing beam splitter 46 are changed to directions at +90° and 0° with respect to the reference direction.

That is, in this embodiment, a transmitted beam 41b from a non-polarizing glass member 41 is incident on the second polarizing beam splitter 46 through a λ/4 plate 42a to be divided into light components polarized in directions at 90° and 0° with respect to the reference direction. Since optical intensities I1 to I4 based on beams polarized in different directions are obtained by light-receiving units 15a to 15d, substantially the same effects as those of the embodiment shown in FIG. 23 can be obtained.

Figure 26:
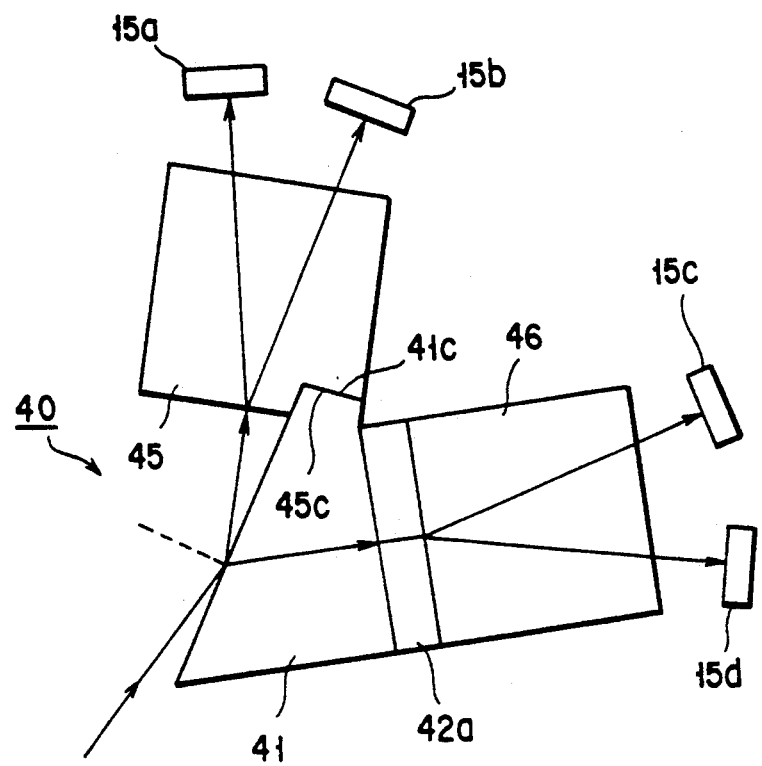
FIG. 26 is a view showing the structure of the composite beam splitter in detail.

FIG. 26 is a detailed illustration of the joining portion between a non-polarizing glass member 41 and a first polarizing beam splitter 45 in a composite beam splitter 40 in still another embodiment of the present invention. In this embodiment, a stepped portion 45c is formed on part of the incident surface of the first polarizing beam splitter 45 such that an upper surface 41c of the non-polarizing glass member 41 is fitted in the stepped portion 45c. By forming such an engaging portion, alignment with the optical axis can be more accurately performed, and the composite beam splitter 40 can be formed firmly.

Note that, as a wave plate for relatively changing the phases of two beams, a single λ/4 plate may be used as in the embodiment shown in FIG. 1. In addition, a wave plate may be inserted in each optical path, as in the embodiment shown in FIG. 6. Furthermore, although not shown, wave plates may be arranged in the same optical path.

As has been described above, in the measuring method for ellipsometric parameters and the ellipsometer according to the present invention, a reflected beam having an elliptically polarized light component reflected by a measurement target is divided into four different polarized light components, and the optical intensities of the polarized light components are detected, thereby calculating ellipsometric parameters on the basis of the four optical intensities. Unlike the conventional method, therefore, the analyzer need not be rotated, and the λ/4 plates need not be inserted/removed in/from optical paths of beams input/output to/from a measurement target.

The optical measurement system can be constituted by only stationary members, and the time required to move movable members can be saved so that ellipsometric parameters can be measured almost instantly by one measuring operation. Therefore, even if measurement targets move, ellipsometric parameters and film thickness can be measured in an on-line manner. At the same time, a specific quadrant to which each calculated phase difference belongs can be determined. In addition, high measurement precision can be maintained through a wide range of film thickness.

Furthermore, since no movable portions are present, the overall apparatus can be reduced in size and weight, allowing installation of the apparatus in a narrow place, e.g., a production inspection line of products.

Moreover, by using a composite beam splitter, the overall apparatus can be further reduced in size and weight.

What is claimed is:

1. An ellipsometer comprising:
 a light source section for radiating a polarized beam onto a measurement target at a predetermined angle;
 a composite beam splitter for splitting a reflected beam from the measurement target into four different polarized light components;
 four light-receiving elements for detecting light intensities of the polarized light components into which the reflected beam is split by said composite beam splitter; and
 arithmetic means for calculating ellipsometric parameters of elliptically polarized light components of said reflected beam on the basis of four light optical intensities detected by said four light-receiving elements;
 said composite beam splitter comprising:
  a non-polarizing beam splitter for splitting the reflected light beam from the measurement target into two split beams respectively having two different directions;
  two optical members, each for dividing a corresponding one of said two split beams emerging from said non-polarized beam splitter into two beams, said two beams having polarization directions which differ from each other;
  a wave plate, arranged in an optical path of at least one of said two split beams from said non-polarizing beam splitter which are incident on said two optical members, for changing a phase of one split beam traveling said optical path relative to a phase of the other of said two split beams
  one of said optical members comprising a first polarizing beam splitter, having one end fixed to said non-polarizing beam splitter, for splitting a reflected beam from said non-polarizing beam splitter into light components polarized in directions which differ from each other by 90°; and
  the other of said optical members comprising a second polarizing beam splitter, bonded to an exit surface of said non-polarizing beam splitter, from which a transmitted beam emerges, for splitting the transmitted beam from said non-polarizing beam splitter into light components polarized in directions which differ from each other by 90°.

2. The ellipsometer of claim 1, wherein said wave plate is connected to an incident surface of one of said first and second polarizing beam splitters.

3. The ellipsometer of claim 1, wherein said non-polarizing beam splitter comprises a glass member.

4. The ellipsometer of claim 1, wherein said wave plate is a λ/4 wave plate.

5. An ellipsometer comprising:
 a light source section for radiating a polarized beam onto a measurement target at a predetermined angle;
 a composite beam splitter for spitting a reflected beam from the measurement target into four different polarized light components;
 four light-receiving elements for detecting light intensities of the polarized light components into which the reflected beam is split by said composite beam splitter; and
 arithmetic means for calculating ellipsometric parameters of elliptically polarized light components of said reflected beam on the basis of four light intensities detected by said four light-receiving elements;
 said composite beam splitter comprising:
  a non-polarizing optical element for splitting the reflected light beam from the measurement target, at an incident surface of said non-polarizing optical element, into a reflected beam and a transmitted beam;

a first polarizing beam splitter, having one end fixed to said non-polarizing optical element, into a reflected beam and a transmitted beam;

a first polarizing beam splitter, having one end fixed to said non-polarizing optical element, for splitting the reflected beam from said non-polarizing optical element into light components polarized in directions which differ from each other by 90°;

a second polarizing beam splitter, bonded to an exit surface of said non-polarizing optical element from which the transmitted beam emerges, for splitting the transmitted beam from said non-polarizing optical element into light components polarized in directions which differ from each other by 90°; and a wave plate bonded to an incident surface of one of said first and second polarizing beam splitters.

6. The ellipsometer of claim 5, wherein said non-polarizing optical element comprises a glass member.

7. The ellipsometer of claim 5, wherein said wave plate is a $\lambda/4$ wave plate.

* * * * *